(12) United States Patent
Chen et al.

(10) Patent No.: US 6,664,310 B2
(45) Date of Patent: Dec. 16, 2003

(54) HYDROGENFLUORIDES OF AMINOSILANOLS AND THEIR USE

(75) Inventors: Chia-hung Chen, Dublin, OH (US); Jorg Kroker, Powell, OH (US); Robert B. Fechter, Worthington, OH (US)

(73) Assignee: Ashland Inc., Dublin, OH (US)

( * ) Notice: Subject to any disclaimer, the term of this patent is extended or adjusted under 35 U.S.C. 154(b) by 4 days.

(21) Appl. No.: 10/131,101

(22) Filed: Apr. 24, 2002

(65) Prior Publication Data

US 2003/0004224 A1 Jan. 2, 2003

Related U.S. Application Data

(60) Provisional application No. 60/289,744, filed on May 9, 2001.

(51) Int. Cl.[7] .............................. C08J 3/00; C08K 5/54; C08L 75/00; B22C 1/22; C07F 7/04
(52) U.S. Cl. ....................... 523/139; 164/526; 164/527; 523/142; 523/143; 524/188; 524/589; 524/590; 556/413
(58) Field of Search ................................. 523/139, 142, 523/143; 524/188, 589, 590; 556/413; 164/526, 527

(56) References Cited

U.S. PATENT DOCUMENTS 3,409,579 A * 11/1968 Robins
6,017,978 A    1/2000 Chen et al. .................. 523/143

FOREIGN PATENT DOCUMENTS

| WO | WO 97/40103 | 10/1997 | ........... C08L/83/10 |
| WO | WO 01/41954 | 6/2001 | |

* cited by examiner

*Primary Examiner*—Patrick D. Niland
(74) *Attorney, Agent, or Firm*—David L. Hedden

(57) ABSTRACT

This invention relates to hydrogenfluorides of aminosilanols and their use. The hydrogenfluorides of aminosilanols are formed by the reaction of an aqueous solution of a fluorinated acid, preferably, hydrofluoric acid, with an aminoalkoxysilane. The hydrogenfluorides of aminosilanols are particularly useful in foundry binders, most particularly no-bake and cold-box phenolic urethane foundry binders.

23 Claims, No Drawings

HYDROGENFLUORIDES OF AMINOSILANOLS AND THEIR USE

CROSS-REFERENCE TO RELATED APPLICATIONS

This application is a utility application based on provisional application serial No. 60/289,744 filed on May 9, 2001.

CLAIM TO PRIORITY

Applications claim the priority date of provisional application serial No. 60/289,744 filed on May 9, 2001, which is hereby incorporated by reference.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION (1) Field of the Invention

This invention relates to hydrogenfluorides of aminosilanols and their use. The hydrogenfluorides of aminosilanols are formed by the reaction of an aqueous solution of a fluorinated acid, preferably, hydrofluoric acid, with an aminoalkoxysilane. The hydrogenfluorides of aminosilanols are particularly useful in foundry binders, most particularly no-bake and cold-box phenolic urethane foundry binders.

(2) Description of the Related Art

One of the major processes used in the foundry industry for making metal parts is sand casting. In sand casting, disposable foundry shapes (usually characterized as molds and cores) are made by shaping and curing a foundry binder system that is a mixture of sand and an organic or inorganic binder. The binder is used to strengthen the molds and cores.

Two of the major processes used in sand casting for making molds and cores are the no-bake process and the cold-box process. In the no-bake process, a liquid curing agent is mixed with an aggregate and shaped to produce a cured mold and/or core. In the cold-box process, a gaseous curing agent is passed through a compacted shaped mix to produce a cured mold and/or core. Phenolic urethane binders, cured with a gaseous tertiary amine catalyst, are often used in the cold-box process to hold shaped foundry aggregate together as a mold or core. See for example U.S. Pat. No. 3,409,579. The phenolic urethane binder system usually consists of a phenolic resin component and polyisocyanate component which are mixed with sand prior to compacting and curing to form a foundry binder system. Because the foundry mix often sits unused for extended lengths of time, the binder used to prepare the foundry mix must not adversely affect the benchlife of the foundry mix.

Among other things, the binder must have a low viscosity, be gel-free, remain stable under use conditions, and cure efficiently. The cores and molds made with the binders must have adequate tensile strengths under normal and humid conditions, and release effectively from the pattern. Binders, which meet all of these requirements, are not easy to develop.

Because the cores and molds are often exposed to high temperatures and humid conditions, it also desirable that the foundry binders provide cores and molds that have a high degree of humidity resistance. This is particular important for foundry applications, where the core or mold is exposed to high humidity conditions, e.g. during hot and humid weather, or where the core or mold is subjected to an aqueous core-wash or mold coating application for improved casting quality.

Phenolic urethane cold-box and no-bake foundry binders often contain a silane coupling agent and/or aqueous hydrofluoric acid to improve humidity resistance. See for example U.S. Pat. No. 6,017,978. The silane and hydrofluoric acid are typically added to the phenolic resin component of the binder.

However, the addition of the silane and free aqueous hydrofluoric acid in phenolic urethane binders often results in one or more problems. For instance, the hydrofluoric acid usually requires special handling procedures, particularly because it is known to etch vitreous materials, e.g. flow control sight tubes commonly used in pipe line systems to convey the binder from storage to its point of use. In the case of phenolic urethane no-bake binders, the use of the silane and hydrofluoric acid slows the chemical reaction, and thus increases the worktime of the foundry mix and the striptime of the core or mold. If a longer time is required for the sand mix to set, this negatively affects productivity. In the case of the phenolic urethane cold-box binders, a precipitate may form over time in the phenolic resin component, particularly when the solvent package for the phenolic resin component contains non-polar solvents. The formation of a precipitate is undesirable because it requires disposal and adversely affects the storage and performance of the binder.

All citations referred to under this description of the "Related Art" and in the "Detailed Description of the Invention" are expressly incorporated by reference.

BRIEF SUMMARY OF THE INVENTION

This invention relates to certain hydrogenfluorides of aminosilanols and their use. The hydrogenfluorides of aminosilanols have the following structural formula:

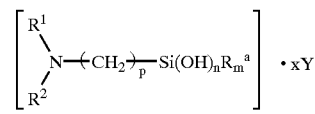

wherein:

(1) $R^1$ and $R^2$ are selected from the group consisting of H; alkyl groups, aryl groups, substituted alkyl groups, aryl groups, mixed alky-aryl groups; di- or triamino groups, amino alkyl groups, amino aryl groups, amino groups having mixed alky-aryl groups, and amino groups having substituted alkyl groups, aryl groups, mixed alky-aryl groups; aminocarbonyl groups; and alkylsilanol groups, preferably where at least one of the $R_1$ and $R_2$ groups is H and the other group is an unsubstituted alkyl group having 1–4 carbon atoms;

(2) n is a whole number from 1 to 3, preferably where $n \geq 1$;

(3) n+m=3;

(4) p is a whole number from 1 to 5, preferably 2 to 3

(5) $R^a$ is selected from the group consisting of alkyl groups, aryl groups, mixed alky-aryl groups, substituted alkyl groups, aryl groups, mixed alkyl-aryl groups, preferably an unsubstituted alkyl group having from 1–4 carbon atoms;

(6) x is a number and is equal to 0.1 and 3 per nitrogen atom of the aminosilanol, and is preferably from 1 to 2.5 per nitrogen atom in the aminoalkoxysilane; and (7) Y=HF or HF complex, which results from a compound that hydrolyzes to yield HF, for instance ammonium fluoride, ammoniumbifluoride, potassium bifluoride, tetrafluoroboric acid, hexafluorophosphoric acid, hexafluorosilicic acid, N,N-diisopropyl aminetris (hydrogenfluoride), N,N'-dimethyl-2-imidazolidone-hexakis(hydrogenfluoride), preferably HF.

The compositions contain little or no free fluorinated acid. An unexpected advantage of the hydrogenfluorides of an aminoalkoxysilane is that they can be dried, packaged as a powder, transported, and then redissolved in a solvent at the site where they are used without loss of activity, even though they are hydrolysis products of aminoalkoxysilanes. This reduces or eliminates the handling problems associated with using fluorinated acids, such as hydrogen fluoride.

The hydrogenfluorides of aminosilanols are particularly useful in foundry binders, most particularly no-bake and cold-box phenolic urethane foundry binders. Phenolic urethane no-bake binders containing the hydrogenfluorides of aminosilanols have excellent humidity resistance, and this is achieved without substantial adverse effects on the reactivity of the binder. Phenolic urethane cold-box binders containing the hydrogenfluorides of aminosilanols also have excellent humidity resistance. In some cases, there is an additional advantage with respect to phenolic urethane cold-box binders. Certain phenolic urethane cold-box binders, which contain a diaminoalkoxysilane and non polar solvents, do not etch glass and show improved stability, i.e. they form little or no solid precipitate over an extended shelf life.

In contrast to the approaches shown in the prior art, where either HF or an aminosilane is used alone or in combination, the hydrogenfluorides of aminosilanols are the reaction product of a fluorinated acid (preferably HF), water, and aminoalkoxysilanes.

BRIEF DESCRIPTION OF THE SEVERAL VIEWS OF THE DRAWINGS

Not Applicable.

DETAILED DESCRIPTION OF THE INVENTION

The detailed description and examples will illustrate specific embodiments of the invention and will enable one skilled in the art to practice the invention, including the best mode. It is contemplated that many equivalent embodiments of the invention will be operable besides those specifically disclosed.

The hydrogenfluorides of aminosilanols are the reaction products formed by the reaction of an aqueous solution of a fluorinated acid, either hydrofluoric acid or a fluorinated acid, which hydrolyzes to yield hydrofluoric acid, with a aminoalkoxysilanes. Preferably, the fluorinated acid is hydrofluoric acid, most preferably an aqueous solution of hydrofluoric acid, containing from 10 to 90 weight percent water, preferably 30–60 weight percent water. Other fluorinated acids that can be used are ammoniumfluoride, ammoniumbifluoride, potassiumbifluoride, tetrafluoroboric acid, hexafluorophosphoric acid, hexafluorosilicic acid, N,N-diisopropylaminetris(hydrogenfluoride), and N,N'-dimethyl-2-imidazolidone-hexakis(hydrogenfluoride).

The aminoalkoxysilanes used to prepare the hydrogenfluorides of the aminosilanols have the following structural formula:

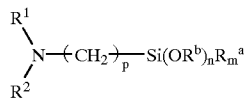

wherein:
(1) $R^1$ and $R^2$ are selected from the group consisting of H; alkyl groups, aryl groups, mixed alky-aryl groups, substituted alkyl groups, aryl groups; di- or triamino groups, amino alkyl groups, amino aryl groups, amino groups having mixed alky-aryl groups, and amino groups having substituted alkyl groups, aryl groups, mixed alky-aryl groups; aminocarbonyl; and alkoxysilane groups, where $R^1$ and $R^2$ can be the same or different and preferably where at least one of the $R^1$ and $R^2$ groups is H, and the other group is an unsubstituted alkyl group having 1–4 carbon atoms;
(2) n is a whole number from 1 to 3, preferably where $n \geq 1$;
(3) n+m=3;
(4) p is a whole number from 1 to 5, preferably 2 to 3, and
(5) $R^a$ and $R^b$ are selected from the group consisting of alkyl groups, aryl groups, mixed alky-aryl groups, substituted alkyl groups, aryl groups, preferably an unsubstituted alkyl group having from 1–4 carbon atoms, and can be identical or different.

Specific examples of aminoalkoxysilanes include 3-aminopropyldimethyl-methoxysilane, 3-aminopropyltrimethoxysilane, 3-aminopropyl-triethoxysilane, 3-aminopropylmethyl-dimethoxysilane 3-aminopropylmethyl-diethoxysilane, N-(n-butyl)-3-aminopropyl-trimethoxysilane, N-aminoethyl-3-aminopropylmethyl-dimethoxysilane, 3-ureidopropyltrimethoxysilane, 3-ureido-propyltriethoxysilane, N-phenyl-3-aminopropyl-trimethoxysilane, N-[(N'-2-aminoethyl)-2-aminoethyl)]-3-aminopropyltrimethoxysilane and bis (3-trimethoxy-silylpropyl) amine.

The fluorinated acid and/or the aminoalkoxysilane may contain a polar solvent. Examples of polar solvents include, for example, water, methanol, ethanol, isopropanol and butanol; ethylene and propylene carbonate; ethylene glycol, propylene glycol, and ethers thereof; isophorone; tetrahydrofuran, dioxolane, 4-methyl dioxolane and 1,3-dioxepane. Typically the amount of solvent is from 0 to 1000, preferably 10 to 300 weight percent based on the weight of the aminoalkoxysilane.

The hydrogenfluorides of aminosilanols are prepared by reacting a fluorinated acid with the aminoalkoxysilane, typically in a plastic reaction vessel, preferably at temperatures of 10° C. to 70° C. and preferably at atmospheric pressure. The fluorinated acid is gradually added to the aminoalkoxysilane and the mixture is stirred gently. A modest exotherm results, and eventually a thin and clear liquid is obtained. The reaction product is tested for free fluorinated acid by bringing into contact with glass to see whether it etches the glass. The stoichiometrical ratio of fluorine of the fluorinated acid to nitrogen of the aminoalkoxysilane is from 0.1:1.0 to 3.0:1.0, preferably from 1.0:1.0 to 2.5:1.0.

The hydrogenfluorides of aminosilanols are particular useful additives for phenolic urethane foundry binders. These binders are well known in the art and commercially available. They contain a phenolic resin component and a polyisocyanate component, which are cured in the presence of a tertiary amine catalyst. The amount of hydrogenfluoride of an aminoalkoxysilane added to a phenolic urethane binder is from 0.1–10.0 weight percent, based on the weight of the phenolic resin component, preferably from 0.15 to 2.0 weight percent.

The phenolic resin component comprises a phenolic resole resin, which is preferably prepared by reacting an excess of aldehyde with a phenol in the presence of either an alkaline catalyst or a metal catalyst. The phenolic resins are preferably substantially free of water and are organic solvent soluble. The preferred phenolic resins used in the subject binder compositions are well known in the art, and are specifically described in U.S. Pat. No. 3,485,797, which is hereby incorporated by reference. These resins, known as benzylic ether phenolic resole resins, are the reaction products of an aldehyde with a phenol. They contain a preponderance of bridges joining the phenolic nuclei of the polymer, which are ortho-ortho benzylic ether bridges. They are prepared by reacting an aldehyde and a phenol in a mole ratio of aldehyde to phenol of at least 1:1 in the presence of a metal ion catalyst, preferably a divalent metal ion such as zinc, lead, manganese, copper, tin, magnesium, cobalt, calcium, and barium.

The phenols use to prepare the phenolic resole resins include any one or more of the phenols which have heretofore been employed in the formation of phenolic resins and which are not substituted at either the two ortho-positions or at one ortho-position and the para-position. These unsubstituted positions are necessary for the polymerization reaction. Any of the remaining carbon atoms of the phenol ring can be substituted. The nature of the substituent can vary widely and it is only necessary that the substituent not interfere in the polymerization of the aldehyde with the phenol at the ortho-position and/or para-position. Substituted phenols employed in the formation of the phenolic resins include alkyl-substituted phenols, aryl-substituted phenols, cyclo-alkyl-substituted phenols, aryloxy-substituted phenols, and halogen-substituted phenols, the foregoing substituents containing from 1 to 26 carbon atoms and preferably from 1 to 12 carbon atoms.

Specific examples of suitable phenols include phenol, 2,6-xylenol, o-cresol, p-cresol, 3,5-xylenol, 3,4-xylenol, 2,3,4-trimethyl phenol, 3-ethyl phenol, 3,5-diethyl phenol, p-butyl phenol, 3,5-dibutyl phenol, p-amyl phenol, p-cyclohexyl phenol, p-octyl phenol, 3,5-dicyclohexyl phenol, p-phenyl phenol, p-crotyl phenol, 3,5-dimethoxy phenol, 3,4,5-trimethoxy phenol, p-ethoxy phenol, p-butoxy phenol, 3-methyl-4-methoxy phenol, and p-phenoxy phenol. multiple ring phenols such as bisphenol A are also suitable.

The aldehyde used to react with the phenol has the formula RCHO wherein R is a hydrogen or hydrocarbon radical of 1 to 8 carbon atoms. The aldehydes reacted with the phenol can include any of the aldehydes heretofore employed in the formation of phenolic resins such as formaldehyde, acetaldehyde, propionaldehyde, furfuraldehyde, and benzaldehyde. The most preferred aldehyde is formaldehyde.

The phenolic resin used must be liquid or organic solvent-soluble. The phenolic resin component of the binder composition is generally employed as a solution in an organic solvent. The amount of solvent used should be sufficient to result in a binder composition permitting uniform coating thereof on the aggregate and uniform reaction of the mixture. The specific solvent concentration for the phenolic resins will vary depending on the type of phenolic resins employed and its molecular weight. In general, the solvent concentration will be in the range of up to 80% by weight of the resin solution and preferably in the range of 20% to 80%.

The polyisocyanate component of the binder typically comprises a polyisocyanate and organic solvent. The polyisocyanate has a functionality of two or more, preferably 2 to 5. It may be aliphatic, cycloaliphatic, aromatic, or a hybrid polyisocyanate. Mixtures of such polyisocyanates may be used. Also, it is contemplated that chemically modified polyisocyanates, prepolymers of polyisocyanates, and quasi prepolymers of polyisocyanates can be used. Optional ingredients such as release agents may also be used in the polyisocyanate hardener component.

Representative examples of polyisocyanates which can be used are aliphatic polyisocyanates such as hexamethylene diisocyanate, alicyclic polyisocyanates such as 4,4'-dicyclohexylmethane diisocyanate, and aromatic polyisocyanates such as 2,4' and 2,6-toluene diisocyanate, diphenylmethane diisocyanate, and dimethyl derivates thereof. Other examples of suitable polyisocyanates are 1,5-naphthalene diisocyanate, triphenylmethane triisocyanate, xylylene diisocyanate, and the methyl derivates thereof, polymethylenepolyphenyl isocyanates, chlorophenylene-2,4-diisocyanate, and the like.

The polyisocyanates are used in sufficient concentrations to cause the curing of the phenolic resin when gassed with the curing catalyst. In general the polyisocyanate ratio of the polyisocyanate to the hydroxyl of the phenolic resin is from 1.25:1 to 1:1.25, preferably about 1:1. Expressed as weight percent, the amount of polyisocyanate used is from 10 to 500 weight percent, preferably 20 to 300 weight percent, based on the weight of the phenolic resin.

The polyisocyanate is used in a liquid form. Solid or viscous polyisocyanate must be used in the form of organic solvent solutions. In general, the solvent concentration will be in the range of up to 80% by weight of the resin solution and preferably in the range of 20% to 80%.

Those skilled in the art will know how to select specific solvents for the phenolic resin component, and in particular the solvents required in the polyisocyanate component. It is known that the difference in the polarity between the polyisocyanate and the phenolic resins restricts the choice of solvents in which both components are compatible. Such compatibility is necessary to achieve complete reaction and curing of the binder compositions of the present invention. Polar solvents of either the protic or aprotic type are good solvents for the phenolic resin, but have limited compatibility with the polyisocyanate. Aromatic solvents, although compatible with the polyisocyanate, are less compatible with the phenolic results. It is, therefore, preferred to employ combinations of solvents and particularly combinations of aromatic and polar solvents.

Examples of aromatic solvents include xylene and ethylbenzene. The aromatic solvents are preferably a mixture of aromatic solvents that have a boiling point range of 125° C. to 250° C. The polar solvents should not be extremely polar such as to become incompatible with the aromatic solvent. Suitable polar solvents are generally those which have been classified in the art as coupling solvents and include furfural, furfuryl alcohol, cellosolve acetate, butyl cellosolve, butyl carbitol, diacetone alcohol, and "Texanol".

The solvent component can include drying oils such as disclosed in U.S. Pat. No. 4,268,425. Such drying oils include glycerides of fatty acids which contain two or more double bonds. Also, esters of ethylenically unsaturated fatty acids such as tall oil esters of polyhydric alcohols or monohydric alcohols can be employed as the drying oil. In addition, the binder may include liquid dialkyl esters such as dialkyl phthalate of the type disclosed in U.S. Pat. No. 3,905,934 such as dimethyl glutarate, dimethyl succinate; and mixtures of such esters.

Although not required when the hydrogenfluoride of an aminosilanol is used, the binder may also contain a silane (typically added to the phenolic resin component) having the following general formula:

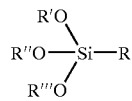

wherein R', R" and R"' are hydrocarbon radicals and preferably an alkyl radical of 1 to 6 carbon atoms and R is an alkyl radical, an alkoxy-substituted alkyl radical, or an alkyl-amine-substituted alkyl radical in which the alkyl groups have from 1 to 6 carbon atoms, and can be identical or different. The silane is preferably added to the phenolic resin component in amounts of 0.01 to 5 weight percent, preferably 0.1 to 1.0 weight percent based on the weight of the phenolic resin component.

When preparing an ordinary sand-type foundry shape, the aggregate employed has a particle size large enough to provide sufficient porosity in the foundry shape to permit escape of volatiles from the shape during the casting operation. The term "ordinary sand-type foundry shapes," as used herein, refers to foundry shapes which have sufficient porosity to permit escape of volatiles from it during the casting operation.

The preferred aggregate employed for ordinary foundry shapes is silica wherein at least about 70 weight percent and preferably at least about 85 weight percent of the sand is silica. Other suitable aggregate materials include zircon, olivine, aluminosilicate, sand, chromite sand, and the like. Although the aggregate employed is preferably dry, it can contain minor amounts of moisture.

In molding compositions, the aggregate constitutes the major constituent and the binder constitutes a relatively minor amount. In ordinary sand type foundry applications, the amount of binder is generally no greater than about 10% by weight and frequently within the range of about 0.5% to about 7% by weight based upon the weight of the aggregate. Most often, the binder content ranges from about 0.6% to about 5% by weight based upon the weight of the aggregate in ordinary sand-type foundry shapes.

The binder compositions are preferably made available as a two-package system with the phenolic resin component in one package and the polyisocyanate component in the other package. Usually, the phenolic resin component is first mixed with sand and then the polyisocyanate component is added. Methods of distributing the binder on the aggregate particles are well-known to those skilled in the art.

The foundry binder system is molded into the desired shape, such as a mold or core, and cured. Curing by the cold-box process takes place by passing a volatile tertiary amine, for example dimethylethylamine, dimethylpropylamine, dimethylisopropylamine, and preferably triethyl amine, through the shaped mix as described in U.S. Pat. No. 3,409,579. Curing by the no-bake process takes place by mixing a liquid amine curing catalyst into the foundry binder system, shaping it, and allowing it to cure, as described in U.S. Pat. No. 3,676,392. Useful liquid amines have a $pK_b$ value generally in the range of about 5 to about 11. Specific examples of such amines include 4-alkyl pyridines, isoquinoline, arylpyridines, 1-vinylimidazole, 1-methylimidazole, 1-methylbenzimidazole, and 1,4-thiazine. Preferably used as the liquid tertiary amine catalyst is an aliphatic tertiary amine, particularly 4-phenylpropylpyridine. In general, the concentration of the liquid amine catalyst will range from about 0.2 to about 10.0 percent by weight of the phenolic resin, preferably 1.0 percent by weight to 4.0 percent by weight, most preferably 2.0 percent by weight to 3.5 percent by weight based upon the weight of the phenolic resin.

The following abbreviations and components are used in the Examples:

Abbreviations

The following abbreviations are used:
A-1160 an ureidoalkoxysilane manufactured by OSi Specialties, a business of Crompton Corporation.
A-187 an epoxy silane manufactured by OSi Specialties a business of Crompton Corporation.
BOS based on sand.
Dynasylan 1411 a diaminoalkoxysilane manufactured by Sivento, a subsidiary of Degussa-Huels Corp., and having the same chemical composition as A-2120.
ISOCURE® 372F/672 F Binder a phenolic urethane cold-box foundry binder manufactured by Ashland Specialty Chemical Company, a division of Ashland Inc.
PEP SETS 1670/2670 binder a phenolic urethane no-bake binder manufactured by Ashland Specialty Chemical Company, a division of Ashland Inc., cured with PEP SET& 3501 liquid tertiary amine curing catalyst
% RH relative humidity %.
Silquest A-2120 a diaminoalkoxysilane manufactured by OSi Specialties a business of Crompton Corporation, and having the same chemical composition as Dynasylan 1411.
ST striptime, used in connection with the no-bake process for core/mold-making, is defined as the time elapsed between mixing the binder components and the sand and placing the sand mix in a pattern, and when the foundry shape reaches a level of 90 on the Green Hardness "B" Scale Gauge sold by Harry W. Dietert Co.
WT worktime, used in connection with the no-bake process for core-making, is defined as the time elapsed between mixing the binder components and when the foundry shape reaches a level of 60 on the Green Hardness "B" Scale Gauge sold by Harry W. Dietert Co., Detroit, Mich.

EXAMPLES

While the invention has been described with reference to preferred embodiments, those skilled in the art will understand that various changes may be made and equivalents may be substituted for elements thereof without departing from the scope of the invention. In addition, many modifications may be made to adapt a particular situation or material to the teachings of the invention without departing from the essential scope thereof. Therefore, it is not intended that the invention be limited to the particular embodiments disclosed herein, but that the invention will include all embodiments falling within the is scope of the appended claims. All amounts and percentages are by weight, unless otherwise expressly indicated.

Examples 1–7 and Comparative Example A

Examples 1–7 illustrate the preparation of several hydrogenfluorides of aminosilanols. The hydrogenfluorides of aminosilanols are formed by the reaction of HF (49% concentration in water) and the aminoalkoxysilanes specified in Table I, which are 50% solutions in methanol. To make the hydrogenfluoride of the aminoalkoxysilane, the solution of aminoalkoxysilane in methanol was added to a plastic container, and then the HF (49% concentration in water) was added gradually and gently at room temperature, and mixed well. In Examples 1–3, a ureidoalkoxysilane in was used, while in examples 4–7, a diaminoalkoxysilane was used.

A modest exothermic was observed, and the mixture was allowed to cool. The mixture was stored overnight to allow complete reaction. A water-thin clear liquid was obtained, which was tested to ensure no free HF exists, by placing a gram of the product into a glass container to determine whether the glass etched. If the glass does not etch, this indicates that there is no free HF in the product. The components used to make the hydrogenfluorides of aminosilanols are set forth in Table I.

TABLE I (Preparation of hydrogenfluorides of aminosilanols)

| Example silane | Commercial silane | Weight ratio HF/silane solution | F/N molar ratio |
|---|---|---|---|
| 1 | A-1160 | 10/50 | 1.09 |
| 2 | A-1160 | 15/50 | 1.63 |
| 3 | A-1160 | 20/50 | 2.18 |
| 4 | Dynasylan 1411 | 20/50 | 2.02 |
| 5 | Dynasylan 1411 | 10/50 | 1.01 |
| 6 | Dynasylan 1411 | 12/50 | 1.22 |
| 7[1] | Silquest A 2120 | 14/50 | 1.62 |
| A | A-187 | 10/50 | — |

[1]In this example the amount of A-2120 in the methanol solution was about 62%.

[1]In this example the amount of A-2120 in the methanol solution was about was 62%.

The structure of the hydrogenfluorides of aminosilanols of Examples 1–7 were characterized by MALDI mass spectrometry, NMR, and acid-base titration. The results indicated that the products were hydrogenfluorides of aminosilanols.

Example 8–9 and B

Use of a Dried and Reconstituted Hydrogenfluoride of an Aminosilanol in a phenolic urethane Binder to Prepare Cores by the Cold-box Process The hydrogenfluoride of the aminosilanol of Example 7 was dried by evaporating 40.0 g. of solution in a dessicator under vacuum over a bed of anhydrous calcium sulfate (Drierite) at room temperature until a constant weight was achieved. The dried product was a tan, friable, amorphous solid weighing 18.6 g. The dried product was then reconstituted as an aqueous solution by dissolving 6.06 g. of the dried product in 5 g. of methanol and 2 g. of water (hereinafter referred to as the "reconstituted product"). The hydrogenfluoride of the aminosilanol of Example 7 and the reconstituted product were then used to make test foundry cores by the cold-box process. Example 8 contained 1% of the solution of the hydrogen fluoride of the aminosilanol of Example 7, and Example 9 contained 1% of the reconstituted product. Example B is a comparison example where 0.3 % of hydrofluoric acid (49%) and 0.5% of aminoalkoxysilane A-2120 were added separately.

Several test cores were prepared with the phenolic urethane binders. One hundred parts of binder (Part I first and then Part II) were mixed with Wedron 540 silica sand such that the weight ratio of Part I to Part II was 55/45 and the binder level was 1.0% by weight BOS. The resulting foundry mix is forced into a dogbone-shaped corebox by blowing it into the corebox. The shaped mix in the corebox is then contacted with triethyl amine at 20 psi for 1 second, followed by a 6 second nitrogen purge at 40 psi., thereby forming tensile strength test specimen ("dog bones") using the standard procedure.

The tensile strengths of the test cores made according to the examples were measured on a Thwing Albert Intellect II instrument. Tensile strengths were measured on freshly mixed sand (zero bench), and sand aged for three hours (3-hour bench). Tensile strengths of test cores made with the sand mixes were measured immediately (Imm.), 5 minutes, 1 hour, and 24 hours after removing them from the corebox. In order to check the resistance of the test cores to degradation by humidity, some of the test cores were stored in a humidity chamber for 24 hours at a humidity of 90 percent relative humidity before measuring the tensile strengths. Measuring the tensile strength of the test core enables one to predict how the mixture of sand and polyurethane-forming binder will work in actual foundry operations. Lower tensile strengths for the test cores indicate inferior binder performance. The results are set forth in Table II.

TABLE II (Tensile strengths of test cores made with a phenolic urethane binder, containing a reconstituted hydrogen fluoride of aminosilanol, by the cold-box process)

| Additive | 8 Example 7 | 9 Reconstituted Example 7 | B HF/Silane Separately |
|---|---|---|---|
| Tensile Strengths of Test Cores (psi) zero-bench | | | |
| I mm | 98 | 103 | 107 |
| 5 min | 128 | 126 | 165 |
| 1 hr | 138 | 188 | 169 |
| 24 hrs | 180 | 190 | 172 |
| 24 hr + 90% RH | 48 | 61 | 69 |

Examples 8 and 9 show that the dried and reconstituted hydrogenfluoride of aminosilanol of Example 7 works at as well as, or better, than the originally prepared solution of the hydrogenfluoride of aminosilanol of Example 6. The usefulness of the dried hydrogenfluoride of aminosilanol is significant because it can be transported easily and is ready to use for a variety of applications. Comparison Example B indicates that both the original solution of the hydrogenfluoride of the aminosilanol and the reconstituted product are comparable to the separate addition of hydrofluoric acid and diaminosilane with respect to humidity resistance. However, neither the original solution of the hydrogenfluoride of the aminosilanol nor the reconstituted product have the handling problems associated with the use of free hydrofluoric acid.

Example 10 and Comparative Examples C and D

Use of hydrogenfluoride of a ureidosilanol in a phenolic urethane Binder to Prepare Test Cores by the No-bake Process This example illustrates the effect of using the hydrogenfluorides of aminosilanols of Example 1 in a phenolic urethane no-bake binder PEP SET® 1670/2670 binder at a 55/45 mix ratio. The binder level was 1.3 weight percent BOS and the catalyst level was 3 weight percent PEP SET® 3501 liquid amine curing catalyst, based on the weight of Part I. Foundry mixes were prepared by first mixing 4000 parts WEDRON 540 silica sand with the phenolic resin component and the liquid catalyst for about 2 minutes. Then the polyisocyanate component was added and mixed for about 2 minutes. The sand mix was rammed into a test pattern, which produced a test cores in accordance with AFS# 329–87-S, known as the "Briquette Method". The tensile strengths of the test cores were measured.

Example 10 contains 0.7% of the hydrogen fluoride of the aminosilanol of Example in the phenolic resin component of the binder. Comparative Example F does not contain HF or aminoalkoxysilane. Comparative Example G contains 0.56% of A-1160 aminoalkoxysilane and 0.14% HF (49% in water), added separately as described in U.S. Pat. No. 6,017,978.

The worktime and striptime of the sand mix, and the tensile strengths of the test cores are shown in the Table III.

TABLE III (Tensile strengths of cores made with phenolic urethane, containing a hydrogenfluoride of an aminosilanol, by the no-bake process)

| Example | 10 | C | D |
|---|---|---|---|
| WT/ST (min) | 6:15/8:30 | 3:45/4:45 | 8:15/10:45 |
| Tensile strength (psi) | | | |
| ½ hr | 133 | 121 | 115 |
| 1 hr | 194 | 170 | 173 |
| 3 hrs | 234 | 227 | 229 |
| 24 hrs | 350 | 280 | 341 |
| 24 hrs + 90% RH | 301 | 99 | 310 |

The results set forth in Table III indicate that the binders of Example 10 provided test cores with improved humidity resistance when compared to the Comparative Example C (no aminoalkoxysilane and no HF). Although the humidity resistance of the test cores made with the binder of Example 10 and Comparative Example D were similar, the work time of the foundry mix and strip time of the cores made with the binder or Example 10 were significantly less than when the binder of Comparative Example D was used. This indicates that improved humidity resistance was achieved without the drastic increase in work time and strip time, which occurs when HF and aminoalkoxysilane were added separately. Increased work time and strip time negatively impact the productivity of the binder. Thus, these examples indicate that the hydrogenfluoride of the aminosilanol provide improved humidity resistance while maintaining good productivity.

Example 11 and Comparative Examples E–G

Use of hydrogenfluoride of a ureidodisilanol in a phenolic urethane Binder to Prepare Cores by the Cold-box Process The hydrogenfluoride of the ureidodisilanol of Example 1 was tested in a phenolic urethane cold-box binder. A two-component phenolic urethane cold-box foundry binder ISO-CURE® 372F/672F was selected. Comparative Example E is a control and does not contain HF, a silane, or the ureidodisilanol of Example 1. Comparative Example F contains the ureidodisilanol, A-1160 (0.5% by weight), in the phenolic resin component of the binder, but does not contain HF. Comparative Example G contains HF (0.2% by weight) in the phenolic resin component of the binder, but does not contain a silane. Example 11 contains the hydrogenfluoride of the ureidodisilanol of Example 1 (0.8% by weight) in the phenolic resin component of the binder.

Several test cores were prepared according to the procedure in Example 8, except the weight ratio of Part I to Part II was 53/47 and the binder level was 1.5% by weight BOS. The results are set forth in Table IV.

TABLE IV (Tensile strengths of test cores made with a phenolic urethane binder by the cold-box process)

|  | E | F | G | 11 |
|---|---|---|---|---|
| Tensile Strengths of Test Cores (psi) zero-bench | | | | |
| 1 mm | 169 | 163 | 156 | 166 |
| 5 min | 185 | 217 | 197 | 254 |
| 1 hr | 196 | 211 | 196 | 255 |
| 24 hrs | 207 | 261 | 221 | 269 |
| 24 hr + 90% RH | 31 | 48 | 32 | 104 |
| 3-hour bench | | | | |
| 1 mm | 124 | 151 | 134 | 140 |
| 24 hrs | 163 | 227 | 192 | 255 |
| 24 hrs + 90% RH | 44 | 46 | 41 | 101 |

The test results in Table IV indicate that the test cores, prepared with the binder containing the hydrogen fluoride of the aminosilanol of Example 1, had better humidity resistance (bold numbers for tensile strengths of test cores maintained in at a relative humidity of 90% for 24 hours before measuring tensile strengths) than the test cores prepared with the binders of Examples E–G for sand mixes, prepared immediately after mixing (zero bench) and three hours after mixing. The test results also indicate that the foundry mix containing the hydrogenfluoride of the aminosilanol had good benchlife.

Example 12 and H–I

Use of Other hydrogenfluorides of a diaminosilanol in a phenolic urethane Cold-box Binder Example 11 was repeated, except the hydrogen fluoride of the aminosilanol used was the one defined in Example 4 (prepared with a diaminoalkoxysilane). Binder H is a control and did not contain HF, a silane, or a hydrogen fluoride of an aminosilanol. Binder I is comparison binder containing the reaction product of silane A-187 (an epoxysilane) with HF (the binder of Example A). The results are set forth in Table V.

TABLE V (Tensile strengths in psi of test cores and humidity resistance)

| Example | H | I | 12 |
|---|---|---|---|
| Tensile Strengths of Test Cores (psi) zero-bench | | | |
| 1 mm | 169 | 186 | 177 |
| 5 min | 185 | 221 | 231 |
| 1 hr | 196 | 240 | 251 |
| 24 hrs | 207 | 221 | 290 |
| 24 hr + 90% RH | 31 | 65 | 104 |
| 3-hour bench | | | |
| 1 mm | 124 | 135 | 143 |
| 24 hrs | 163 | 222 | 242 |
| 24 hrs + 90% RH | 44 | 82 | 117 |
| 5-hour bench | | | |
| 1 mm | 127 | 122 | 126 |
| 24 hrs | 146 | 196 | 222 |
| 24 hrs + 90% RH | 34 | 64 | 91 |

The data in Table V indicate that the test cores prepared form the binder containing the epoxysilane/HF combination did not give satisfactory humidity resistance. On the other hand, the test cores of the binder containing the hydrogenfluoride of the diaminosilanol derived from Dynasylan 1411 (Example 4) had excellent humidity resistance. These examples indicate that the amino functional group of the aminoalkoxysilane is important in achieving improved humidity resistance. The test results also indicate that the foundry mix containing the hydrogenfluoride of the aminosilanol had good benchlife.

We claim:

1. A hydrogenfluoride of an aminosilanol having the following structural formula:

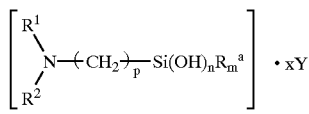

wherein:
(a) $R^1$ and $R^2$ are selected from the group consisting of H; alkyl groups, aryl groups, mixed alky-aryl groups, substituted alkyl groups, aryl groups; di- or triamino groups, amino alkyl groups, amino aryl groups, amino groups having mixed alky-aryl groups, and amino groups having substituted alkyl groups, aryl groups, mixed alky-aryl groups; aminocarbonyl groups; and alkylsilanol groups;
(b) n is a whole number from 1 to 3.
(c) n+m=3;
(d) $R^a$ is selected from the group consisting of alkyl groups, aryl groups, mixed alkyl-aryl groups, and substituted alkyl, aryl, and mixed alkyl-aryl groups.
(e) x is a number which equals from 0.1 to 3.0 per nitrogen atom in the aminosilanol; and
(f) Y=HF or HF complex.

2. The hydrogenfluoride of an aminosilanol of claim 1 wherein at least one of the $R^1$ and $R^2$ groups is H and the other group is an unsubstituted alkyl group having 1–3 carbon atoms.

3. The hydrogenfluoride of an aminosilanol of claim 1 wherein where n≧1.

4. The hydrogenfluoride of an aminosilanol of claim 1 wherein $R^a$ is selected from the group consisting of unsubstituted alkyl group having from 1–4 carbon atoms.

5. The hydrogenfluoride of an aminosilanol of claim 1 wherein Y is HF.

6. The hydrogenfluoride of an aminosilanol of claim 1 wherein x is 1.

7. A hydrogenfluoride of an aminosilanol prepared by reacting an aqueous solution of hydrofluoric acid, or a compound that hydrolyzes to hydrofluoric acid, and an aminoalkoxysilane at temperatures of 10° C. to 70° C. such that the molar ratio of fluorine of the hydrofluoric acid to nitrogen of the alkoxyaminosilane is from 0.1:1.0 to 3.0:1.0.

8. A hydrogenfluoride of an aminosilanol prepared in accordance with claim 7, such that the reaction is carried out at atmospheric pressure.

9. A hydrogenfluoride of an aminosilanol prepared in accordance with claim 8 wherein the reaction is carried out in the presence of a polar solvent.

10. A foundry binder system comprising:
(a) a phenolic resin component; and
(b) a polyisocyanate component
wherein component (a) contains from 0.1 to 10 percent of a hydrogenfluoride of an aminosilanol of claim 1, 2, 3, 4, 5, or 6, wherein the amount of hydrogenfluoride of aminosilanol is based on the weight of the phenolic resin in the phenolic resin component.

11. The foundry binder system claim 10 wherein the phenolic resin component comprises a (a) a polybenzylic ether phenolic resin prepared by reacting an aldehyde with a phenol such that the molar ratio of aldehyde to phenol is from 1.1:1 to 3:1 in the presence of a divalent metal catalyst, and (b) a solvent in which the resole resin is soluble.

12. The foundry binder system of claim 11 wherein the phenol is selected from the group consisting of phenol, o-cresol, p-cresol, and mixtures thereof.

13. The foundry binder system of claim 12 wherein the aldehyde is formaldehyde.

14. The foundry binder system of claim 13 wherein the NCO content of the polyisocyanate component is from 12% to 33%.

15. The foundry binder system of claim 14 wherein the ratio of hydroxyl groups of the polybenzylic ether phenolic resin to the polyisocyanate groups of the polyisocyanate hardener is from 0.80:1.2 to 1.2:0.80.

16. The foundry binder system of claim 15 wherein the divalent metal catalyst used to prepare the phenolic resin is zinc.

17. A foundry mix comprising:
A. a major amount of an aggregate; and
B. an effective bonding amount of the binder system of claim 10.

18. A process for preparing a foundry shape which comprises:
(a) forming a foundry mix as set forth in claim 17;
(b) forming a foundry shape by introducing the foundry mix obtained from step (a) into a pattern;
(c) contacting the shaped foundry binder system with a tertiary amine catalyst; and
(d) removing the foundry shape of step (c) from the pattern.

19. The process of claim 18 wherein the amount of said binder composition is about 0.4 percent to about 5.0 percent based upon the weight of the aggregate.

20. The process of claim 19 wherein the tertiary amine catalyst is a gaseous tertiary amine catalyst.

21. The process of claim 19 wherein the tertiary amine catalyst is a liquid tertiary amine catalyst.

22. The process of casting a metal which comprises:
(a) preparing a foundry shape in accordance with claim 20;
(b) pouring said metal while in the liquid state into and around said shape;
(c) allowing said metal to cool and solidify; and
(d) then separating the molded article.

23. The process of casting a metal which comprises:
(a) preparing a foundry shape in accordance with claim 22;
(b) pouring said metal while in the liquid state into and around said shape;
(c) allowing said metal to cool and solidify; and
(d) then separating the molded article.

* * * * *